United States Patent [19]

Weinberger

[11] Plant 4,902

[45] Oct. 26, 1982

[54] PLUM TREE

[75] Inventor: John H. Weinberger, Fresno, Calif.

[73] Assignee: Superior Farming Company, Bakersfield, Calif.

[21] Appl. No.: 246,301

[22] Filed: Mar. 23, 1981

[51] Int. Cl.[3] ..... A01H 5/00
[52] U.S. Cl. ..... Plt./38
[58] Field of Search ..... Plt./38

*Primary Examiner*—James R. Feyrer
*Attorney, Agent, or Firm*—Roger B. Webster

[57] ABSTRACT

A plum tree which is of medium size, medium vigor, upright-spreading, open, and round-topped; foliated with medium size, obovate, abruptly pointed leaves having a crenate margin, and small, green, opposite, globose glands; flowers from pointed, free buds of medium size and length; the flowers being medium in season, medium size, and white; and is a regular and very productive bearer of large, globose, symmetrical, semi-freestone fruit uniform both in size and form, the fruit having burgundy red skin, red flesh with a yellow tinge near the base, and a red pit cavity.

1 Drawing Figure

BACKGROUND OF THE VARIETY

1. Field of the Invention.

In the conduct of an extensive plant breeding program — on behalf of a commercial farming company, and in such company's experimental orchard located near Fresno, Fresno County, Calif. — I have originated a substantial number of new and distinct varieties of fruit trees, and which include the present variety of plum tree.

2. Classification of the Variety.

The present variety of plum tree is embraced by Class 38, Plants, of the U.S. Patent Office Manual of Classification.

3. Prior Varieties.

Among existing varieties of plum trees which are known to me, and mentioned herein, are the Angeleno (U.S. Plant Pat. No. 2,747), Queen Ann (unpatented), and Frontier (unpatented).

ORIGIN OF THE VARIETY

The present variety of plum tree was originated by me as an open pollinated seedling of the Angeleno plum tree. A number of such seedlings were grown to fruition, in the aforesaid experimental orchard, under careful and continuing observation by me; the present variety being a selection from such seedlings which evidenced commercial promise.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of plum tree is, characteristically, of medium size, medium vigor, upright-spreading, open, and round-topped; foliated with medium size, obovate, abruptly pointed leaves having a crenate margin, and small, green, opposite, globose glands; flowers from pointed, free buds of medium size and length; the flowers being medium in season, medium size, and white; and is a regular and very productive bearer of large, globose, symmetrical, semi-freestone fruit uniform both in size and form, the fruit having burgundy red skin, red flesh with a yellow tinge near the base, and a red pit cavity.

The present variety of plum tree is further characterized by attractive, red-flesh fruit of excellent eating quality and having a mild, delicate flavor; this in contrast to yellow-flesh plums which are normally acid in flavor.

The fruit of the present variety, while most nearly resembling the Queen Ann in appearance, ripens approximately a week earlier, and the red flesh is in contrast to the yellow flesh of the Queen Ann.

In comparison with the red-flesh fruit of the Frontier, the fruit of the present variety ripens somewhat earlier and has a less prominent apex.

BRIEF DESCRIPTION OF THE DRAWING

The drawing is an illustration, by photographic reproduction in color, of a twig with leaves, and separate fruit; one of the fruit being cut in half to expose the flesh and with the stone remaining in one of the halves.

DESCRIPTION OF THE VARIETY

The botanical details of this new and distinct variety of plum tree — with color definitions (except those in common color terms) referenced to Plochere Color System (in book form) — are as follows:

Tree:
- *Size.*—Medium.
- *Vigor.*—Medium.
- *Growth.*—Upright-spreading.
- *Density.*—Open.
- *Form.*—Round-topped.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—New wood: Green. Dull. Mature wood: Brown.

Leaves:

*Size.*—Medium. Average length — 10.8 cm. Average width — 4.7 cm.
*Form.*—Obovate. Abruptly pointed.
*Thickness.*—Medium.
*Color.*—Medium green.
*Texture.*—Smooth.
*Margin.*—Crenate.
*Petiole.*—Medium length. Medium thickness.
*Glands.*—Average number — 2. Opposite. Small. Globose. Green. Positioned on base of blade.
*Stipules.*—Many remain. Length range — up to 8 mm.

Flower buds:
*Size.*—Medium.
*Length.*—Medium.
*Form.*—Pointed. Free.

Flowers:
*Date of full bloom.*—Feb. 26th, 1980. Medium, as compared with other varieties.
*Size.*—Medium.
*Color.*—White.

Fruit:
*Maturity when described.*—Firm ripe — July 11th, 1980.
*Date of first picking.*—July 7th, 1980.
*Date of last picking.*—July 15th, 1980.
*Size.*—Uniform. Large. Average diameter axially — 56 mm. Average transversely in suture plane — 63 mm.
*Form.*—Uniform. Symmetrical. Globose.
*Suture.*—A distinct but somewhat inconspicuous line extending from base to beyond apex.
*Ventral surface.*—Rounded slightly.
*Lips.*—Nearly equal.
*Cavity.*—Rounded — circular. Average depth — 9 mm. Average breadth — 18 mm.
*Base.*—Rounded.
*Apex.*—Short.
*Pistil point.*—Apical.

Skin:
*Thickness.*—Medium.
*Texture.*—Medium.
*Tenacity.*—Tenacious to flesh.
*Tendency to crack.*—None in wet-dry season.
*Color.*—Burgundy red (Plate 18 — No. 417 — Old Burgundy).
*Down.*—Wanting.

Flesh:

*Color.*—Red (Plate 17 — No. 403 — Raspberry glace) with yellow tinge near base. Surface of pit cavity: Red.
*Amygdalin.*—Wanting.
*Juice.*—Moderate.
*Texture.*—Medium. Meaty.
*Fibers.*—Few. Tender.
*Ripens.*—Evenly.
*Flavor.*—Mild. Delicate.
*Aroma.*—Wanting.
*Eating quality.*—Best.

Stone:
*Type.*—Semi-free. Adheres to flesh along both dorsal and ventral edges.
*Fibers.*—Short.
*Size.*—Small. Average length — 21 mm. Average breadth — 17 mm. Average thickness — 9 mm.
*Form.*—Globose.
*Base.*—Straight.
*Hilum.*—Narrow. Oval.
*Apex.*—Acuminate.
*Sides.*—Equal.
*Surface.*—Slightly ridged near base.
*Ridges.*—Jagged. Interrupted.
*Ventral edge.*—Thin, with wing throughout.
*Dorsal edge.*—Narrow. Shallow. Narrow groove toward base.
*Color.*—Brown (Plate 14 — No. 314 — Bronzio).
*Tendency to split.*—Slight in wet-dry season.

Use: Market.
Keeping quality: Good.
Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, particularly characterized by the regular and very productive bearing of large, globose, symmetrical, semi-freestone fruit uniform both in size and form, the fruit having burgundy red skin, red flesh with a yellow tinge near the base, and a red pit cavity; the fruit, of mild, delicate flavor, most nearly resembling the yellow-flesh fruit of the Queen Ann but ripens approximately a week earlier, and also somewhat earlier than the red-flesh fruit of the Frontier.

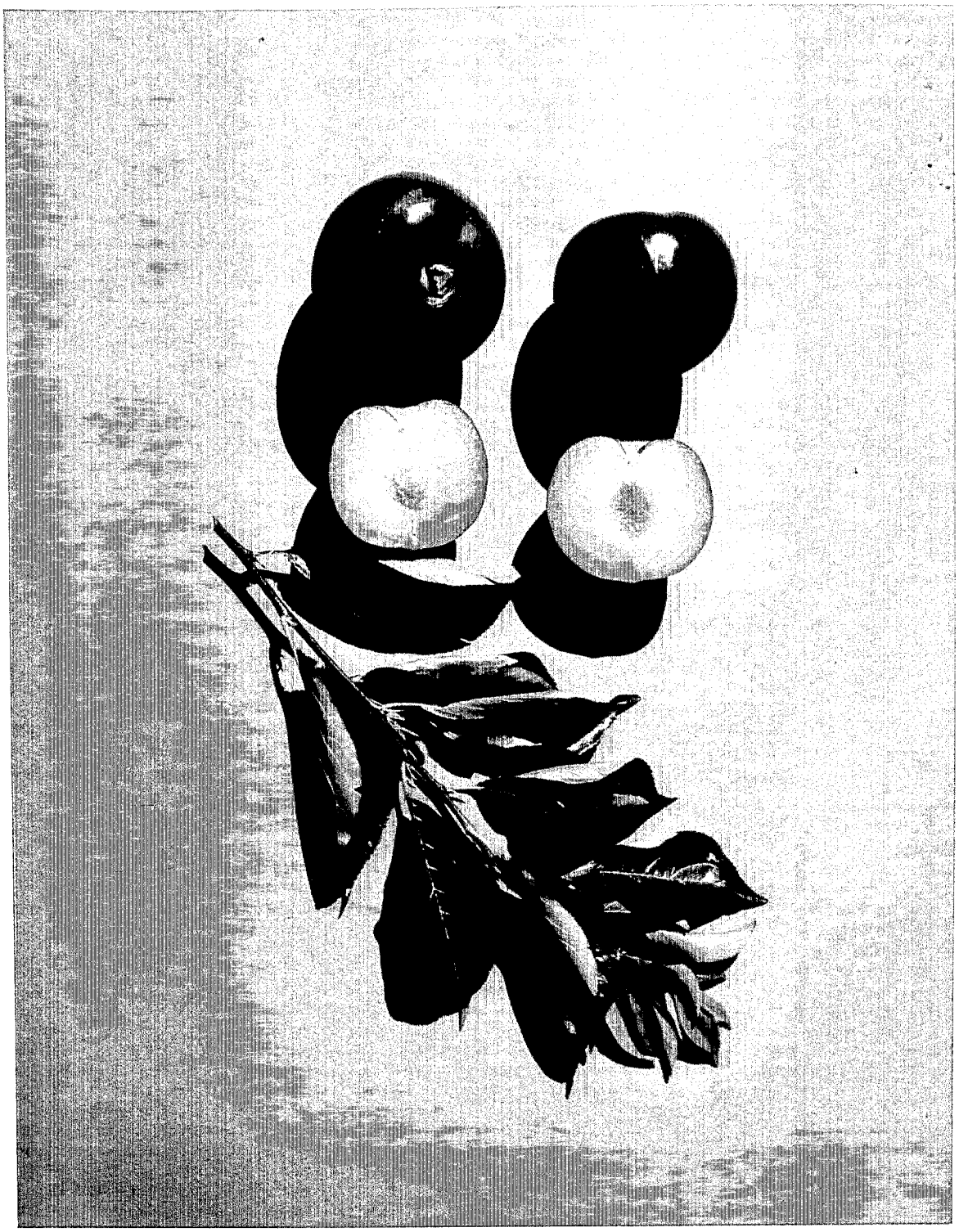

* * * * *